US011364084B2

(12) United States Patent
Govari et al.

(10) Patent No.: US 11,364,084 B2
(45) Date of Patent: Jun. 21, 2022

(54) CONTACT FORCE COMPENSATION IN A ROBOT MANIPULATOR

(71) Applicant: Biosense Webster (Israel) Ltd., Yokneam (IL)

(72) Inventors: Assaf Govari, Haifa (IL); Andres Claudio Altmann, Haifa (IL); Vadim Gliner, Haifa (IL); Yehuda Algawi, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 323 days.

(21) Appl. No.: 16/198,432

(22) Filed: Nov. 21, 2018

(65) Prior Publication Data

US 2020/0155249 A1     May 21, 2020

(51) Int. Cl.
| | | |
|---|---|---|
| *A61B 34/32* | (2016.01) | |
| *A61B 34/35* | (2016.01) | |
| *A61B 34/00* | (2016.01) | |
| *A61B 90/00* | (2016.01) | |
| *A61B 34/30* | (2016.01) | |
| *B25J 9/16* | (2006.01) | |

(52) U.S. Cl.
CPC .............. *A61B 34/32* (2016.02); *A61B 34/35* (2016.02); *A61B 34/76* (2016.02); *A61B 90/06* (2016.02); *A61B 2034/302* (2016.02); *A61B 2090/065* (2016.02); *B25J 9/1633* (2013.01)

(58) Field of Classification Search
CPC ......... A61B 34/32; A61B 34/35; A61B 34/76; A61B 90/06; A61B 2034/302; A61B 2090/065; A61B 2090/064; A61B 90/50; A61B 2034/2074; A61B 2034/301; A61B 34/20; A61B 2034/2051; A61B 34/74; A61B 34/37; A61B 34/25; A61B 34/30
See application file for complete search history.

(56) References Cited

U.S. PATENT DOCUMENTS

| | | |
|---|---|---|
| 5,794,621 A | 8/1998 | Hogan et al. |
| 7,536,218 B2 | 5/2009 | Govari et al. |
| 8,010,180 B2 | 8/2011 | Quaid et al. |

(Continued)

FOREIGN PATENT DOCUMENTS

| | | |
|---|---|---|
| WO | WO 1996/05768 A1 | 2/1996 |
| WO | WO 2012/018821 | 2/2012 |
| WO | WO 2017/020081 | 2/2017 |

OTHER PUBLICATIONS

European Search Report dated Feb. 28, 2020 from corresponding European Patent Application No. 19210417.2.

(Continued)

*Primary Examiner* — Abby Y Lin
*Assistant Examiner* — Dylan M Katz
(74) *Attorney, Agent, or Firm* — Frost Brown Todd LLC

(57) ABSTRACT

A robotic manipulator is attachable to a proximal end of a medical instrument. A processor linked to the manipulator transmits control signals to the manipulator to cause the manipulator to displace the medical instrument to achieve a desired position and orientation of the medical instrument. A contact force sensor is disposed on the medical instrument and linked to the processor. The control signals are issued by the processor responsively to force indications received from the contact force sensor.

18 Claims, 4 Drawing Sheets

(56) References Cited

U.S. PATENT DOCUMENTS

| | | | |
|---|---|---|---|
| 8,390,438 B2* | 3/2013 | Olson | A61B 34/77 340/407.1 |
| 8,594,799 B2* | 11/2013 | Haller | A61B 34/76 607/57 |
| 8,628,518 B2* | 1/2014 | Blumenkranz | A61B 34/30 606/1 |
| 10,292,780 B2* | 5/2019 | Park | A61B 34/76 |
| 10,517,612 B2 | 12/2019 | Bar-tal | |
| 2009/0076476 A1* | 3/2009 | Barbagli | A61B 5/6885 604/500 |
| 2009/0137952 A1 | 5/2009 | Ramamurthy et al. | |
| 2013/0304258 A1 | 11/2013 | Taylor | |
| 2013/0345718 A1 | 12/2013 | Crawford et al. | |
| 2014/0276760 A1 | 9/2014 | Bonyak et al. | |
| 2015/0112486 A1 | 4/2015 | Larkin et al. | |
| 2015/0342695 A1* | 12/2015 | He | G01L 1/246 606/130 |
| 2017/0128128 A1 | 5/2017 | Saba et al. | |
| 2017/0188993 A1* | 7/2017 | Hamilton et al. | A61B 5/4064 |
| 2017/0258530 A1 | 9/2017 | Govari et al. | |
| 2017/0319289 A1* | 11/2017 | Neff | A61B 90/361 |
| 2018/0116743 A1 | 5/2018 | Burbank et al. | |
| 2018/0125560 A1* | 5/2018 | Saadat | A61F 7/123 |
| 2018/0256247 A1 | 9/2018 | Govari et al. | |
| 2019/0104919 A1* | 4/2019 | Shelton, IV | A61B 90/361 |

OTHER PUBLICATIONS

Kesner, Samuel et al.; "Force Control of Flexible Catheter Robots for Beating Heart Surgery", Robotics and Automation (ICRA), 011 IEEE International Conference on, IEEE, May 9, 2011, pp. 1589-1594.

* cited by examiner

CONTACT FORCE COMPENSATION IN A ROBOT MANIPULATOR

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to manipulators or robots adapted for use in surgery. More particularly, this invention relates to provision of contact force feedback and compensation in manipulators or robots adapted for use in surgery.

2. Description of the Related Art

Robotic manipulators typically comprise a controller that control the motion of surgical instruments at a site, which can be remote from the location of the controller and its operator. One such device is the da Vinci® System, which consists of a surgeon's console that is typically in the same room as the patient, and a patient-side cart with four interactive robotic arms controlled from the console. Three of the arms are for tools that hold objects, and can also act as scalpels, scissors, bovies, or graspers. The surgeon uses the console's master controls to maneuver the patient-side cart's three or four robotic arms. The instruments' jointed-wrist design exceeds the natural range of motion of the human hand; motion scaling and tremor reduction further interpret and refine the surgeon's hand movements. The da Vinci System always requires a human operator, and incorporates multiple redundant safety features designed to minimize opportunities for human error when compared with traditional approaches.

One of the characteristics of many of the current robots used in surgical applications, which make them error prone is that they use an articular arm based on a series of rotational joints. The use of an articular system may create difficulties in arriving at an accurately targeted location because the level of any error is increased over each joint in the articular system. One solution to this difficulty is proposed in U.S. Pat. No. 8,628,518 to Blumenkranz, which proposes an arrangement in which a wireless package on a surgical end effector includes a force sensor.

SUMMARY OF THE INVENTION

According to disclosed embodiments of the invention, a probe is placed in contact with the wall of a cavity such as the ear or nasal cavity of a patient by a robotic manipulator. The probe may be configured to perform a variety of functions, such as visual inspection, radiofrequency ablation, or debriding. A contact force sensor is disposed on the distal end of the probe, and is configured to measure the magnitude and direction of the force acting on the distal end when in contact with the cavity wall. The robotic manipulator is activated to position the probe according to feedback received from the contact force sensor. More specifically, during the activation the probe is moved by the robotic manipulator such that the vector force exerted on the sensor is constant when, for example, there is patient movement. Additionally, the measured values of the vector force can be used to provide tactile feedback to the operator.

There is provided according to embodiments of the invention an apparatus, which includes a manipulator that is attachable to a proximal end of a medical instrument. A processor linked to the manipulator transmits control signals to the manipulator to cause the manipulator to displace the medical instrument to achieve a desired position and orientation of the medical instrument. A contact force sensor is disposed on the medical instrument and linked to the processor. The control signals are issued by the processor responsively to force indications received from the contact force sensor.

According to one aspect of the apparatus, the contact force sensor is disposed on the distal 25 percent of the length medical instrument.

According to a further aspect of the apparatus, the contact force sensor is disposed on the distal end of the medical instrument.

In yet another aspect of the apparatus another contact force sensor is disposed on the medical instrument proximal to the contact force sensor, wherein the control signals are issued by the processor responsively to other force indications received from the other contact force sensor.

Still another aspect of the apparatus includes an interface with the processor, wherein the control signals are modifiable by an operator input via the interface, and a wearable haptic receiver linked to the processor having an actuator that deforms responsively to received haptic signals.

An additional aspect of the apparatus includes a wireless transmitter for transmitting the force indications as the haptic signals to the haptic receiver.

According to one aspect of the apparatus, the haptic signals are transmitted to the haptic receiver via the processor.

According to another aspect of the apparatus, the haptic signals are transmitted to the haptic receiver directly from the contact force sensor.

According to another aspect of the apparatus, the processor is operative to calculate a contact force vector between the medical instrument and a contacting surface.

There is further provided according to embodiments of the invention a method, which is carried out by attaching a manipulator to a proximal end of a medical instrument, linking a processor to the manipulator, transmitting control signals from the processor to the manipulator to cause the manipulator to displace the medical instrument in order to achieve a desired position and orientation of the medical instrument, disposing a contact force sensor linked to the processor on the medical instrument, and issuing the control signals from the processor responsively to force indications received from the contact force sensor.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", and "links", are intended to mean either an indirect or direct connection. Thus, if a first device links to a second device, that connection may be through a direct connection, or through an indirect connection via other devices and connections.

Figure 1:
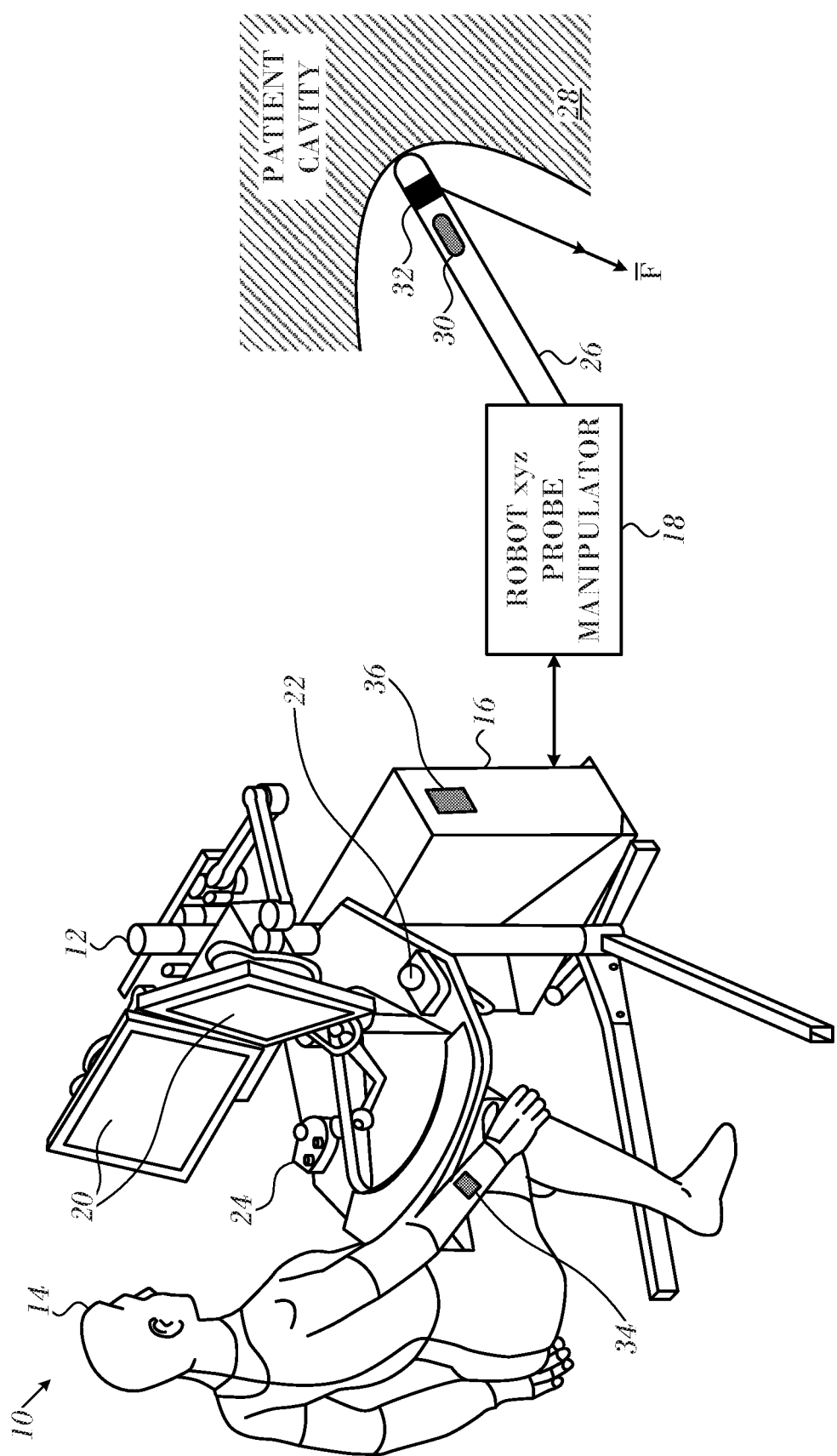
FIG. 1 is a schematic illustration of a robotic medical instrument system, which is constructed and operative in accordance with an embodiment of the invention.

Reference is now made to FIG. 1, which is a schematic illustration of a robotic medical instrument system 10, which is constructed and operative in accordance with an embodiment of the invention. System 10 comprises a console or workstation 12 from which a human operator 14 interacts with a processor 16, which in turn regulates the activities of a manipulator 18. The manipulator 18 is typically located remotely from the workstation 12 and is linked to the processor 16 by cables or wirelessly. The processor 16 presents a graphical user interface on displays 20 and accepts operator input on manipulation devices 22, 24.

The manipulator 18 holds a medical instrument, such as a probe 26, and is capable of manipulating the probe 26 in 3 dimensions (x,y,z) into contact with target tissue 28, which may be the wall of a cavity in the body of the patient. The manipulator 18 may additionally be capable of varying the attitude of the probe 26 about pitch, yaw and roll axes. The location of the probe 26 with respect to a reference coordinate system is established using a location sensor 30, which can be a magnetic sensor of the type described in commonly assigned U.S. patent application Ser. No. 15/708,357, issued as U.S. Pat. No. 10,517,612 on Dec. 31, 2019; U.S. Patent Application Publication No. 2017/0128128, issued as U.S. Pat. No. 10,588,692 on Mar. 17, 2020; and PCT Patent Document WO96105768 by Ben Haim, all of which are herein incorporated by reference. The location sensor 30 may be capable of determining the position of the probe 26 with up to 6 degrees of freedom.

In another embodiment adapted to cardiac instrumentation, the location sensor 30 may be an electrode for an impedance-based locating system, as taught in U.S. Pat. No. 7,536,218, issued to Govari et al., which is herein incorporated by reference.

In any case, the location sensor 30 may communicate with the processor 16 over a wired or wireless connection, as described in the above-noted U.S. patent application Ser. No. 15/708,357, issued as U.S. Pat. No. 10,517,612 om Dec. 31,2019.

The probe 26 is provided with a contact force sensor 32, which is linked to the processor 16 over a wired or wireless connection. Suitable force sensors are described in commonly assigned U.S. Patent Application Publication No. 2017/0258530 by Beeckler et al., issued as U.S. Pat. No. 10,555,776 on Feb. 11, 2020; and commonly assigned copending U.S. patent application Ser. No. 15/452,843 of Govari et al., published as U.S. Patent Publication No. 2018/0256247 on Sep. 13, 2018, the disclosures of which are herein incorporated by reference. Force sensor 32 is disposed on the distal portion of the probe 26 as shown in FIG. 1. The force sensor 32 issues signals from which a force vector $\vec{F}$ is calculated by the processor 16.

Figure 2:
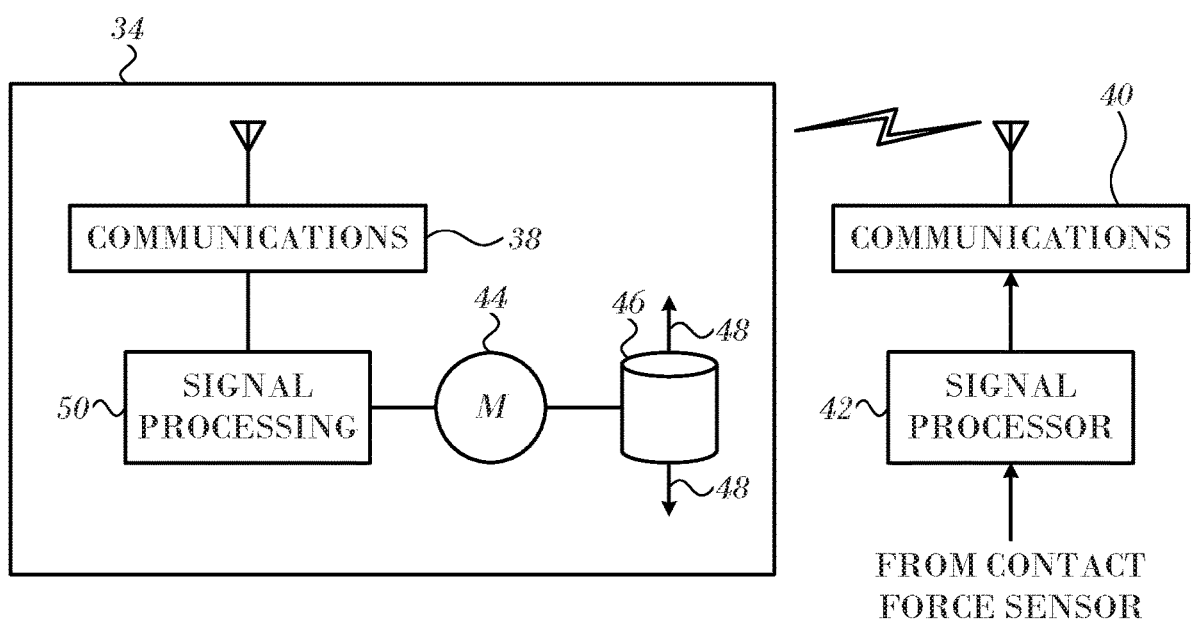
FIG. 2 is a block diagram of a haptic device in the system shown in FIG. 1, which is constructed and operative in accordance with an embodiment of the invention.

In some embodiments, the operator 14 may wear a haptic device 34, such as a wrist bracelet. Data from the force sensor 32 and the location sensor 30 processed by the processor 16. Alternatively, in some embodiments, raw data from the probe 26 may be haptically provided via a haptic device 34 to the operator by the system 10. This arrangement minimizes a need to consult a visual display and avoids distraction caused by an audio alert that might provide contact information. An advantage of this arrangement is shortened reaction time to inappropriate contact force or position of the probe 26. It is often important that the position of the tip of the probe 26 correspond to coordinates of medical images. In one mode of operation raw or processed data from the location sensor 30 may be provided to the haptic device 34. The sensations produced by the haptic device 34 are perceived by the operator as though a virtual assistant were holding his hand while he performs a medical procedure. The processor 16 may include a wireless transmitter 36 that communicates with the haptic device 34, Reference is now made to FIG. 2, which is a block diagram of the haptic device 34, which is wearable by the operator 14, and constructed and operative in accordance with an embodiment of the invention. The haptic device 34 has a wireless communications module 38, which receives signals from another communications module 40. The communications module 40 is linked to the probe 26 (FIG. 1), generally via a signal processor 42. Telemetry signals produced by the signal processor 42 are reflective of the contact force between the probe 26 and the target tissue 28. They are transmitted by the communications module 40 to the communications module 38 using any suitable communications protocol.

Within the haptic device 34 a signal processor 44 has control circuitry linked to an electric motor 44, which drives an actuator 46. The actuator 46 has an oscillatory, vibratory or reciprocating motion, indicated by arrows 48. The tactile sensation experienced by the operator and produced by the actuator 46, e.g., by deforming is representative of the contact force of the probe 26 as communicated via the communications module 38. In operation, the actuator 46 creates a tactile sensation, which the operator can interpret as a measure of the contact force currently being applied by the probe 26 against the target tissue 28. Additionally or alternatively the, signal processor 50 may be configured to control the electric motor 44 so as to cause the actuator 46 to vibrate, the vibrations being felt with a periodicity by the operator whose strength or period correlates with the contact force. Further alternatively, combinations of the intensity, periodicity and intervals of the vibration may communicate the contact force of the probe 26 to the operator 14. Vibratory frequencies varying from about 40 Hz to 250 Hz are suitable to communicate different levels of contact force.

For example, the actuator 46 may vibrate rapidly or slowly according to contact force levels, or may alternate between vibrating and not vibrating to produce tactile silence for perceptibly longer periods, the pattern encoding levels of contact force. In a further example, the actuator 46 may operate for a relatively long and perceptible interval, e.g., 0.25-2 sec, and then cease to operate for a similar interval. Alternatively, specific ranges may produce different sensations, for example as a "step function" of the contact force. Encoding of activity patterns of the actuator 46 in various other ways will occur to those skilled in the art. In any case, such patterns, when haptically perceived by the operator, indicate the magnitude of the catheter's contact force (or other parameter). Additionally or alternatively, the patterns might constitute, for example, a binary signal, indicating whether or not the catheter is in a stable location. The signals may be configurable by the operator, who may choose the kind of feedback he prefers to tactilely receive. Further details of the haptic device 34 are disclosed in commonly assigned U.S. Patent Application Publication No. 20140276760, entitled Force Feedback Device and Method for Catheters, issued as U.S. Pat. No. 9,486,272 on Nov. 8, 2016, which is herein incorporated by reference.

Figure 3:
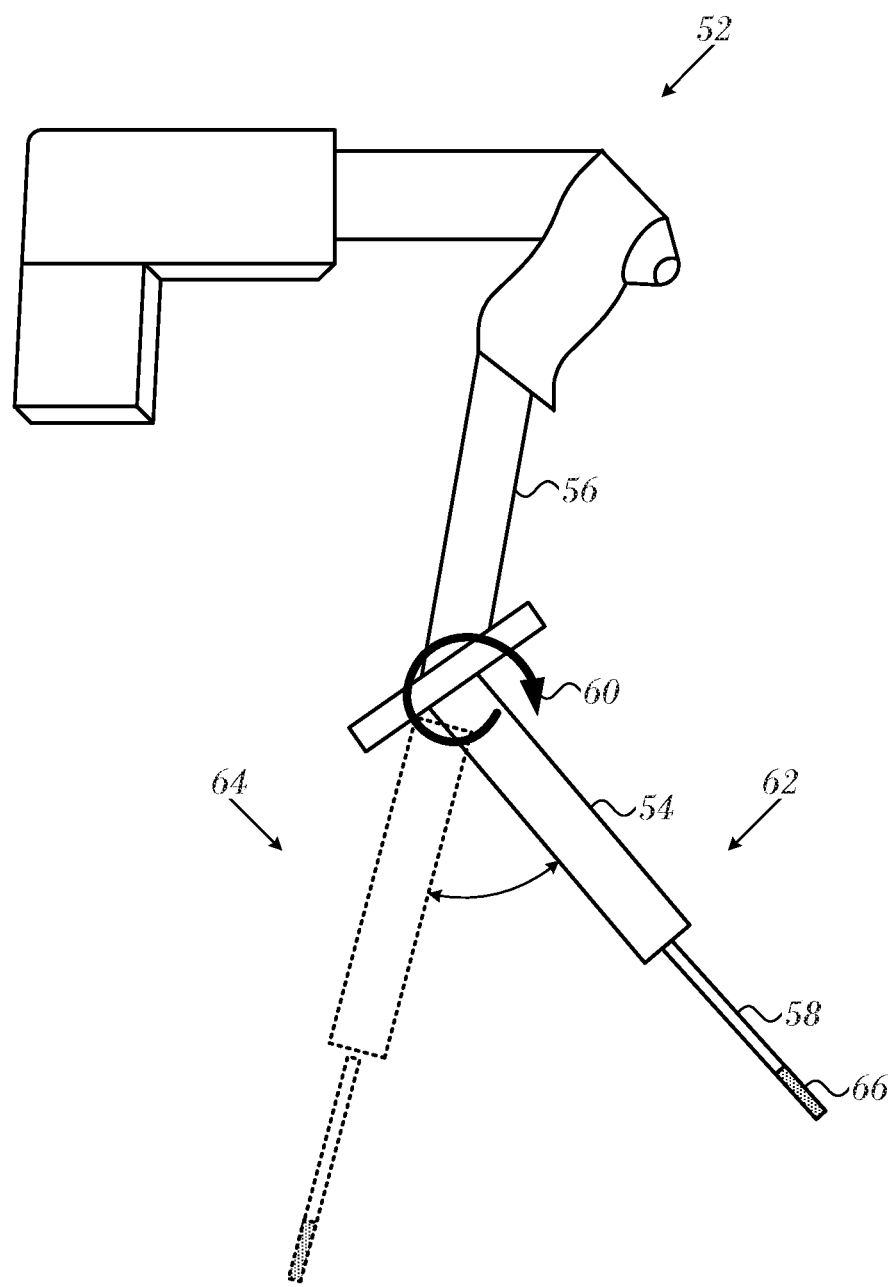
FIG. 3 schematically illustrates a robotic extension, which can be controlled by a manipulator in the system shown in FIG. 1 in accordance with an embodiment of the invention.

Reference is now made to FIG. 3, which schematically illustrates a robotic extension 52 that could be controlled by manipulator 18 (FIG. 1) in accordance with an embodiment of the invention. The extension 52 comprises a distal arm 54, which pivots about a proximal arm 56. The arm 54 grasps a medical instrument 58, such as a probe. In some embodiments the pivoting motion of the arm 54 may be resisted, for example by a spring 60, which causes a restorative motion from a working position 62 to a resting position 64.

Placement of a force sensor 66 distally on the instrument 58 confers an advantage in accuracy and precision of the force measurement compared with placement on the arm 54 of the extension 52. The location of the force sensor 66 on the instrument 58 is application-dependent. It is generally desirable that the force sensor 66 be placed at the most distal location of the instrument 58 that is practical, for example in the distal 25 percent of the length of the instrument 58. Preferably, the instrument 58 is placed at the distal end of the instrument 58. This is due, at least in part to the fact that a sensor disposed on the arm 54 of manipulator 18 experiences a mechanical advantage of force amplification based on a leverage effect, in which a magnitude of movement at the distal end of the probe 26 is exchanged for enhanced force at the arm 54. However any errors would similarly be amplified.

Placement of the force sensor 66 proximal to the distal end causes it to experience a superposition of all forces applied on to the instrument 58 distal to the force sensor 66. For example, an application of a leftward force of 10 grams on the distal tip, and somewhere on the shaft a rightward force of 5 grams, the indicated force will be a superposition of the two. The calculation of the superposition in practice is non-trivial and depends on mechanical structure of the tool, locations of the forces and the position of the force sensor 66. In the case of a flexible instrument, the weight of the segment distal to the force sensor 66 also becomes a factor.

Additionally, the force sensor 66 experiences greater excursion when placed on the instrument 58 as compared with the arm 54. Measurement of such excursion within the force sensor 66 overcomes any jitter that might exist with as a result of the relatively smaller excursion of the arm 54.

Figure 4:
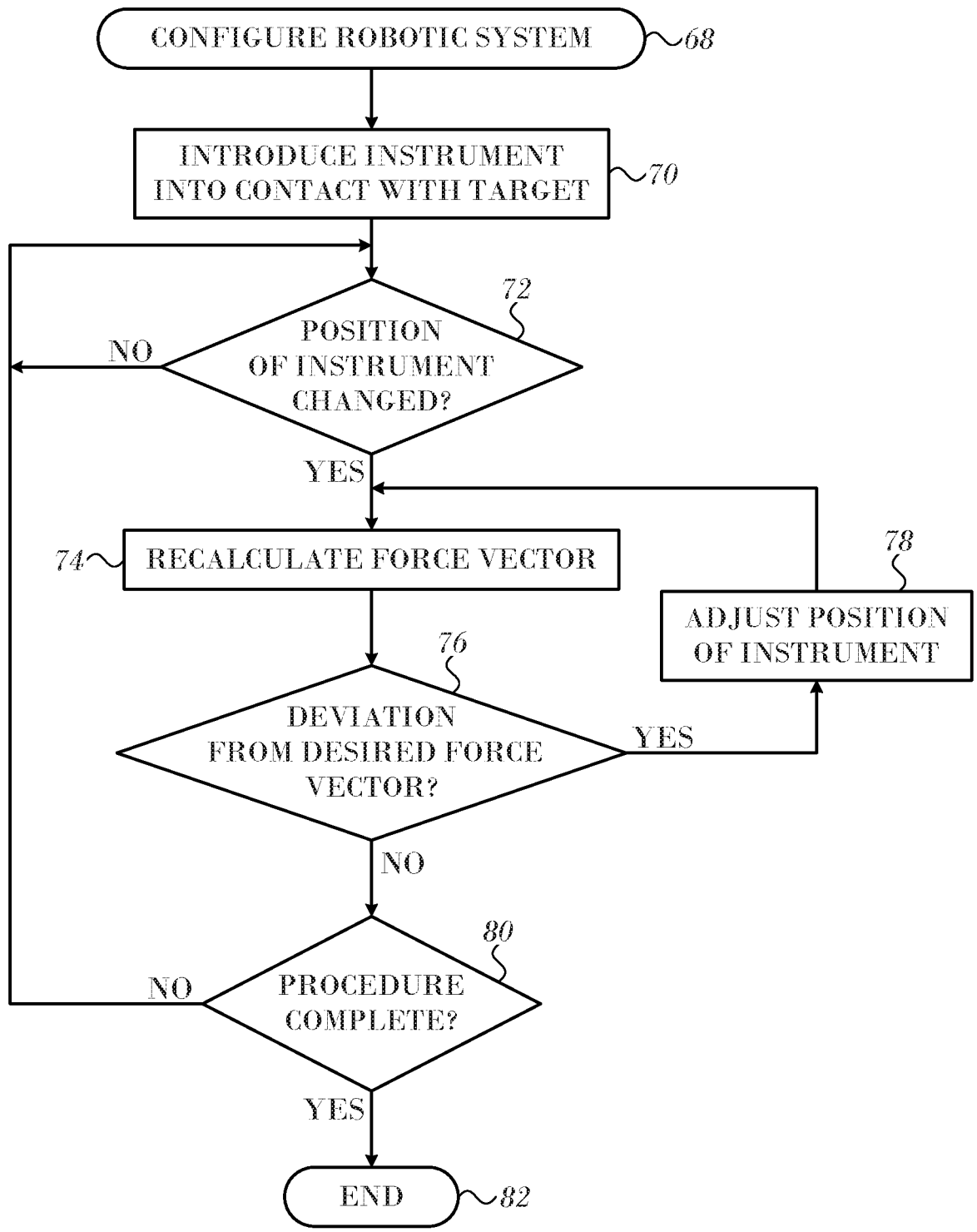
FIG. 4 is a flow chart of a method of operating a robotic medical instrument system in accordance with an embodiment of the invention.

FIG. 4 is a flow chart of a method of operating a robotic medical instrument system in accordance with an embodiment of the invention. At initial step 68 robotic medical instrument system 10 is configured by attachment of a suitable medical instrument to an arm of the manipulator 18. A force sensor is installed at the distal portion of the medical instrument. Optionally, a second force sensor may be placed on a more proximal portion of the medical instrument, which increases the precision of the controlled movements.

Next, at step 70 the probe 26 or other medical instrument is introduced in contact with an operative site of the patient, which is typically a hollow viscous or chamber of an organ such as a paranasal sinus. The introduction may be done using the manipulator 18 (FIG. 1) under guidance of the operator 14. Signals from the force sensor are enabled, and the sensor generates data from which the processor 16 calculates the magnitude and direction of the force vector.

In some embodiments the magnitude and direction of the force vector may be perceived by the operator 14 using a haptic device.

During the operative procedure, the probe 26 may require repositioning by the manipulator 18 at the direction of the operator, which is indicated by delay step 72 in which such requirement is awaited. When the position of the probe 26 changes, the processor 16 then recalculates the force vector at step 74 and determines whether there is a deviation from the desired values of the force vector at decision step 76. If there is such a deviation, then at step 78 the position of the medical instrument is adjusted so as to null out the deviation. Then step 74 is iterated. The feedback loop formed by step 74, decision step 76 and step 78 may iterate until the deviation found in decision step 76 is insignificant, i.e., is less than a predetermined value. Feedback levels are chosen according to the precision needed for a particular medical use, using well known control methods.

When there is no significant deviation found at decision step 76, then, at decision step 80, it is determined if the operative procedure is complete. If the determination at decision step 80 is negative, then control returns to delay step 72 to await another position change in the medical instrument.

If the determination at decision step 80 is affirmative, then the procedure ends at final step 82.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising,
   (a) a medical instrument having a proximal portion and a distal portion, the distal portion having a distal end;
   (b) a manipulator, the proximal portion of the medical instrument being attachable to the manipulator;
   (c) a processor, linked to the manipulator and transmitting control signals to the manipulator to cause the manipulator to displace the medical instrument to achieve a desired position and orientation of the medical instrument within a paranasal passageway of a patient, wherein the processor is further configured to transmit the control signals to the manipulator to cause the manipulator to displace the medical instrument to achieve a predetermined force against the patient;

(d) a first contact force sensor disposed on the distal portion of the medical instrument and linked to the processor, wherein the processor is configured to issue the control signals responsively to force indications received from the first contact force sensor to maintain the predetermined force against the paranasal passageway of the patient;

(e) a location sensor disposed on the distal portion of the medical instrument and linked to the processor, wherein the processor is configured to determine a location of the distal portion based on signals from the location sensor;

(f) a second contact force sensor, the second contact force sensor being positioned proximal to the first contact force sensor on the medical instrument; and (g) a haptic interface device linked to the processor, wherein the processor is configured to transmit haptic signals to the haptic interface device, to thereby drive the haptic interface device, to thereby provide haptic feedback to a human operator, based on signals from the first and second contact force sensors and the location sensor.

2. The apparatus according to claim 1, wherein the distal portion comprises 25 percent of a length of the medical instrument.

3. The apparatus according to claim 1, wherein the first contact force sensor is disposed at the distal end of the medical instrument.

4. The apparatus according to claim 1, wherein the processor is configured to issue the control signals responsively to other force indications received from the second contact force sensor.

5. The apparatus according to claim 1, further comprising:
an operator interface with the processor, wherein the control signals are modifiable by human operator input via the operator interface.

6. The apparatus according to claim 1, further comprising a wireless transmitter for transmitting the haptic signals to the haptic interface device.

7. The apparatus according to claim 6, further comprising a communications module directly coupled with the first contact force sensor, wherein the communications module is configured to transmit the haptic signals to the haptic interface device.

8. The apparatus according to claim 1, wherein the processor is operative to calculate a contact force vector between the medical instrument and a contacting surface.

9. A method, comprising:
(a) attaching a proximal portion of a medical instrument to a manipulator;
(b) linking a processor to the manipulator;
(c) transmitting control signals from the processor to the manipulator to cause the manipulator to displace the medical instrument to achieve a desired position, orientation, and force vector of the medical instrument against a surface of an inner cavity within the head of a patient;
(d) receiving data from a first contact force sensor on the medical instrument, the first contact force sensor being configured to measure force data, the data indicating the force vector measured by the first contact force sensor, the data being received by the processor;

(e) receiving data from a second contact force sensor, the second contact force sensor being positioned proximal to the first contact force sensor on the medical instrument;
(f) receiving data from a location sensor on the medical instrument, the data from the location sensor indicating a location of the medical instrument within a patient;
(g) calculating in the processor a contact force vector between the medical instrument and a contacting surface, wherein the contact force vector is based on the force data received from the first and second contact force sensors and the location indications received from the location sensor;
(h) in response to the data received from the first contact force sensor, the second contact force sensor, and the location sensor, issuing control signals from the processor to constantly maintain the calculated contact force vector of the medical instrument against the surface of the patient during an operation; and
(i) issuing haptic signals from the processor to a haptic interface device, the haptic interface device providing haptic feedback to a human operator in response to the haptic signals, the haptic feedback indicating a magnitude and direction of the calculated contact force vector.

10. The method according to claim 9, wherein the first contact force sensor is disposed on a distal portion of the medical instrument, the distal portion comprising 25 percent of a length of the medical instrument.

11. The method according to claim 9, wherein the first contact force sensor is disposed at a distal end of the medical instrument.

12. The method according to claim 9, further comprising providing an operator interface with the processor, wherein the control signals are modifiable by human operator input via the operator interface.

13. The method according to claim 9, further comprising wirelessly transmitting the force indications as the haptic signals to the haptic receiver.

14. A method, comprising:
(a) attaching a proximal portion of a medical instrument to a manipulator;
(b) linking a processor to the manipulator;
(c) transmitting control signals from the processor to the manipulator to cause the manipulator to displace the medical instrument to achieve a desired position and orientation of the medical instrument, wherein the control signals are received from a human operator via an operator interface;
(d) receiving data from a location sensor on the medical instrument, the data from the location sensor indicating a location of the medical instrument within a patient;
(e) receiving data from a first contact force sensor on a distal end of the medical instrument, the first contact force sensor being configured to measure a force exerted by the medical instrument within a paranasal passageway of a patient, the data indicating the force exerted by the medical instrument, the data being received by the processor;
(f) receiving data from a second contact force sensor, the second contact force sensor being positioned proximal to the first contact force sensor on the medical instrument;
(g) in response to the received data, issuing control signals from the processor so as to maintain a predetermined force of the medical instrument against the paranasal passageway of the patient; and (h) transmitting haptic signals from the medical instrument to a wearable haptic receiver, the wearable haptic receiver having an actuator that deforms responsively to the haptic signals responsively to the force indications received from the first and second contact force sensors and the location indications received from the location sensor.

15. The apparatus according to claim 1, wherein the haptic interface device includes a wearable wrist bracelet having a motor-driven actuator that is configured to deform in response to haptic signals from the processor.

16. The apparatus according to claim 1, wherein the haptic feedback device comprises a vibration generator, the haptic signals being configured to cause the vibration generator to impart vibrations to the human operator with a periodicity or intensity that varies based on signals from the first contact force sensor and the location sensor.

17. The method according to claim 9, wherein the haptic interface device includes a wearable wrist bracelet having a motor-driven actuator that is configured to deform in response to haptic signals from the processor, the actuator deforming to provide the haptic feedback to the human operator in response to the haptic signals.

18. The apparatus according to claim 9, wherein the haptic feedback device comprises a vibration generator, the vibration generator imparting vibrations to the human operator with a periodicity or intensity that varies based on the calculated contact force vector.

* * * * *